(12) United States Patent
Drobe

(10) Patent No.: US 9,885,884 B2
(45) Date of Patent: Feb. 6, 2018

(54) MYOPIA CONTROL OPTICAL SYSTEM

(71) Applicant: ESSILOR INTERNATIONAL (COMPAGNIE GENERALE D'OPTIQUE), Charenton-le-Pont (FR)

(72) Inventor: Bjorn Drobe, Singapore (SG)

(73) Assignee: ESSILOR INTERNATIONAL (COMPAGNIE GENERALE D'OPTIQUE), Charenton-le-Pont (FR)

( * ) Notice: Subject to any disclaimer, the term of this patent is extended or adjusted under 35 U.S.C. 154(b) by 0 days.

(21) Appl. No.: 15/091,073

(22) Filed: Apr. 5, 2016

(65) Prior Publication Data

US 2016/0216537 A1 Jul. 28, 2016

Related U.S. Application Data

(63) Continuation of application No. 14/193,254, filed on Feb. 28, 2014, now abandoned.

(30) Foreign Application Priority Data

Mar. 1, 2013 (EP) .................................... 13305237

(51) Int. Cl.
| | |
|---|---|
| *G02C 7/10* | (2006.01) |
| *G02B 5/22* | (2006.01) |

(Continued)

(52) U.S. Cl.
CPC ............ *G02C 7/105* (2013.01); *A61F 2/1659* (2013.01); *G02B 5/20* (2013.01); *G02C 7/104* (2013.01);

(Continued)

(58) Field of Classification Search
CPC .......... G02C 7/10; G02C 7/104; G02C 7/105; G02C 7/04; G02C 7/044; G02C 2202/24;

(Continued)

(56) References Cited

U.S. PATENT DOCUMENTS

| | | |
|---|---|---|
| 5,233,261 A | 8/1993 | Wajid |
| 6,512,643 B1 | 1/2003 | Wada et al. |

(Continued)

FOREIGN PATENT DOCUMENTS

| | | |
|---|---|---|
| EP | 2267496 | 12/2010 |
| FR | 2958757 | 10/2011 |

OTHER PUBLICATIONS

Communication reporting the extended European Search Report and including the extended European Search Report dated Jul. 5, 2013 for European Patent Application No. EP 13305237.3 (7 pages).

(Continued)

*Primary Examiner* — Jordan Schwartz
(74) *Attorney, Agent, or Firm* — Young & Thompson

(57) ABSTRACT

An optical system having a transmission pattern comprising at least a first zone Z1 extending from at or about 380 nm to a first limit L1 between Z1, and a second zone Z2. A third zone Z3 extends from a second limit L2 between Z2 and Z3 to about 780 nm. L1 may be greater than or equal to or about 436 nm. Second limit L2 may be greater than L1 and smaller than or equal to or about 487 nm. The average transmission values T1, T2, T3, in each zone Z1, Z2, Z3 may be:

$$T2 > 5*(T1+T3)/2, \text{ with}$$

T1 the average transmission over Z1,
T2 the average transmission over Z2,
T3 the average transmission over Z3.
T1 and T3 may be greater than or equal to or about 3% and smaller than or equal to or about 70%. T2 may be greater than or equal to or about 75%.

13 Claims, 1 Drawing Sheet

(51) Int. Cl.
*A61F 2/16* (2006.01)
*G02B 5/20* (2006.01)
*G02B 5/23* (2006.01)
*G02B 5/28* (2006.01)

(52) U.S. Cl.
CPC ..... *A61F 2/1613* (2013.01); *A61F 2250/0082* (2013.01); *G02B 5/223* (2013.01); *G02B 5/23* (2013.01); *G02B 5/28* (2013.01); *G02C 2202/24* (2013.01)

(58) Field of Classification Search
CPC . G02B 5/20; G02B 5/22; G02B 5/223; G02B 5/23; A61F 2/1659; A61F 2/1613; A61F 2250/0082
See application file for complete search history.

(56) References Cited

U.S. PATENT DOCUMENTS

2007/0134474 A1 6/2007 Ahn et al.
2010/0053549 A1 3/2010 Legerton et al.
2015/0070742 A1* 3/2015 Sorek .................. G02B 5/20 359/238
2016/0026005 A1* 1/2016 Flinders .............. G02B 5/22 351/44
2017/0192257 A1* 7/2017 Branda ................ G02F 1/0102

OTHER PUBLICATIONS

M.A. Res et al., "Bandpass filters for use in the visible region", Applied Optics, vol. 16, No. 7, Jul. 1977, pp. 1908-1913.
Regan S. Ashby et al., "The Effect of Bright Light on Lens Compensation in Chicks", Investigative Ophthalmology and Visual Science, vol. 51, No. 10, Oct. 2010 pp. 5247-5253.
Translation of Abstract for FR 2958787 published Oct. 14, 2011 (2 pages).
Wolfgang Wieser, Anaglyph glasses transmission spectra, Apr. 4, 2007, pp. 1-2.

* cited by examiner

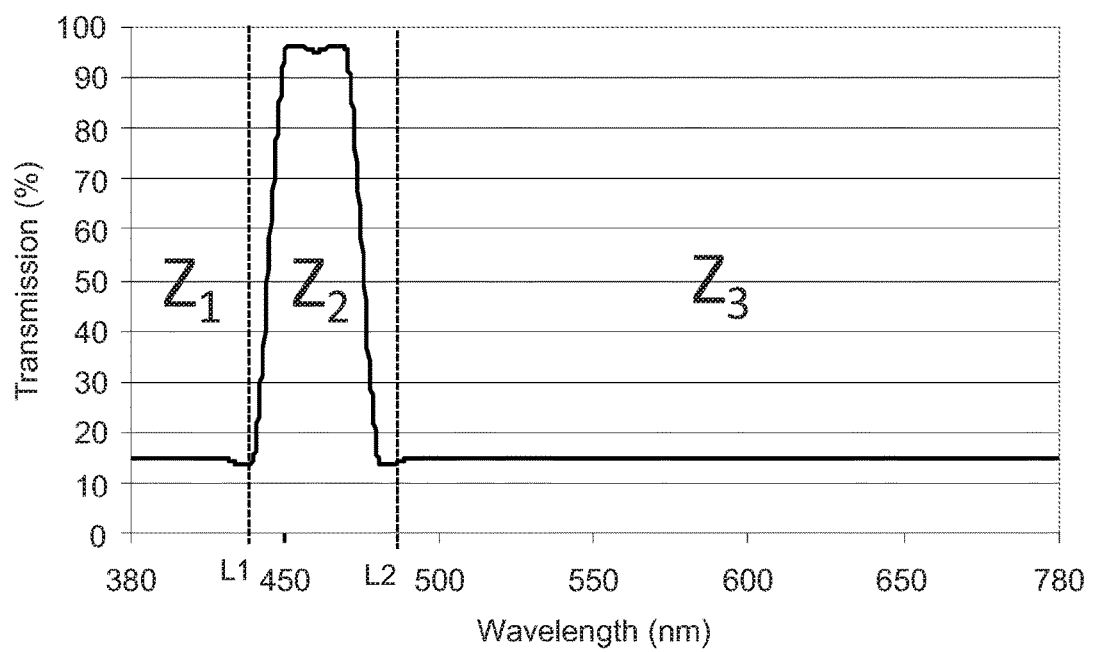

MYOPIA CONTROL OPTICAL SYSTEM

FIELD OF THE INVENTION

The invention relates to an optical system having a transmission pattern specifically adapted to slow down myopia progression of the wearer and to a method for selecting an optical system according to the invention.

BACKGROUND OF THE INVENTION

The discussion of the background of the invention herein is included to explain the context of the invention. This is not to be taken as an admission that any of the material referred to was published, known or part of the common general knowledge at the priority date of any of the claims.

Myopia may have severe long term consequences on the eye that may even result in blindness. It appears that for most individuals, in particular for children, the myopia condition of the eye tends to increase with time.

It is therefore crucial to slow or stop the progression of myopia, as the severity of its consequences is linked to the severity of the final myopia that is reached by the patient.

Recent studies point out natural light can help slow down myopia progression. In particular, it has been observed that outdoors activities slow down myopia progression.

However, when individual and in particular children spend time outdoors, their eyes are also exposed to harmful light (UV, blue light). Solar lenses protect the eyes from the harmful effects of natural light but also appear to decrease the benefits of the outdoor activities on the myopia progression.

Therefore, there is a need for an optical device that provides protection for the eye from the harmful wavelength of natural light and maintains or even enhances the benefit of outdoor activity on myopia progression.

A goal of the present invention is to provide such an optical device.

SUMMARY OF THE INVENTION

In accordance with a first aspect of the invention there is provided an optical system having a transmission pattern comprising at least a first zone Z1 extending from 380 nm to a first limit L1 between the first zone Z1 and a second zone Z2, and a third zone Z3 extending from a second limit L2 between the second zone Z2 and the third zone Z3 to 780 nm, wherein the first limit L1 is greater than or equal to 436 nm and the second limit L2 is greater than the first limit L1 and smaller than or equal to 487 nm; the average transmission values T1, T2, T3, in each zone Z1, Z2, Z3 are such as:

$T2 > 5*(T1+T3)/2$, with

T1 the average transmission over the first zone Z1,
T2 the average transmission over the second zone Z2, and
T3 the average transmission over the third zone Z3,
T1 and T3 being greater than or equal to 3% and smaller than or equal to 70%, and
T2 being greater than or equal to 75%.

Advantageously, the transmission pattern of the optical system according to the invention provides protection from harmful wavelengths of natural light, in the first and third zones and having a greater transmission in the second zone maintains the benefit of outdoor activities on the progression of myopia.

Indeed, the wavelengths comprised in the second zone appear to increase the retinal Dopamine secretion that slow down myopia progression.

Furthermore, the average transmission over the first and second zones is such that the wearer's pupil size in increased when wearing the optical device. Therefore the amount of light the wearer's retina receives in the wavelengths corresponding to the second zone increases. Thus the benefit of outdoor activities on myopia progression is enhanced when using the optical system according to the invention.

According to further embodiments which can be considered alone or in combination:

the first limit L1 is greater than or equal to 446 nm; and/or
the first limit L1 is greater than or equal to 456 nm; and/or
the second limit L2 is smaller than or equal to 477 nm; and/or
the second limit L2 is smaller than or equal to 467 nm; and/or
the average transmission T2 over the second zone Z2 is greater than the average transmissions T1 and T3 over the first and third zones Z1, Z3; and/or
the average transmission T1 over the first zone Z1 is smaller than or equal to the average transmission T3 over the third zone Z3; and/or
the average transmission T1 over the first zone Z1 is greater than or equal to 8% and smaller than or equal to 43%; and/or
the average transmission T1 over the first zone Z1 is greater than or equal to 8% and smaller than or equal to 18%; and/or
the average transmission T3 over the third zone Z3 is greater than or equal to 8% and smaller than or equal to 43%; and/or
the average transmission T3 over the third zone Z3 is greater than or equal to 8% and smaller than or equal to 18%; and/or
the optical system is an optical system selected among the list of optical systems consisting of optical lens, ophthalmic lens, spectacle lens, contact lens, intraocular lens.

The invention further relates to a method for selecting an optical system according to the invention adapted for a wearer, the method comprising the steps of measuring the effect of different optical systems according to the invention on the size of the pupil of the wearer and of selecting the optical system having the greatest average transmission value over the first and third zones and for which the wearer's pupil diameter has increased of at least 0.5 mm when wearing the optical system.

According to a further aspect, the invention relates to the use of an optical system according to the invention to slow down myopia progression of a wearer.

The invention further relates to a method for slowing down myopia progression of a wearer comprising the step of having the wearer wear an optical system according to the invention.

The invention also relates to the optical system according to the invention for slowing down myopia progression of a wearer.

According to a further aspect, the invention relates to a computer program product comprising one or more stored sequences of instructions that are accessible to a processor and which, when executed by the processor, causes the processor to carry out the steps of the method according to the invention.

The invention further relates to a computer readable medium carrying one or more sequences of instructions of the computer program product according to the invention.

Furthermore, the invention relates to a program which makes a computer execute the method of the invention.

The invention also relates to a computer-readable storage medium having a program recorded thereon; where the program makes the computer execute the method of the invention.

The invention further relates to a device comprising a processor adapted to store one or more sequence of instructions and to carry out at least one of the steps of the method according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

DESCRIPTION OF THE DRAWING

Non limiting embodiments of the invention will now be described with reference to the accompanying drawing in which FIG. 1 is an example of a transmission pattern of an optical system according to the invention.

DETAILED DESCRIPTION OF THE EMBODIMENTS

As illustrated on FIG. 1, an optical system according to the invention has a transmission pattern comprising a first, second and third zone Z1, Z2, Z3.

The first zone Z1 extends from 380 nm, for example 400 nm, to a first limit L1 between the first zone Z1 and the second zone Z2.

The third zone Z3 extending from a second limit L2 between the second zone Z2 and the third zone Z3 to 780 nm, for example 700 nm.

The average transmission values T1, T2, T3, in each zone Z1, Z2, Z3 are such as:

$T2 > 5*(T1+T3)/2$, with

T1 the average transmission over the first zone Z1,
T2 the average transmission over the second zone Z2, and
T3 the average transmission over the third zone Z3,
T1 and T3 being greater than or equal to 3% and smaller than or equal to 70%, and
T2 being greater than or equal to 75%.

In the sense of the invention, the "average transmission" over a zone corresponds to average over the corresponding range of wavelength of the percentage of intensity of the incident light within the corresponding range of wavelength that is transmitted through the optical system.

In other words, an average transmission of 70% over the first zone corresponds to 70% of the intensity of the incident light between 380 nm and L1 being transmitted through the optical system.

The inventors have observed an increase in retinal Dopamine secretion by having the first limit L1 greater than or equal to 436 nm and the second limit L2 greater than the first limit L1 and smaller than or equal to 487 nm According to an embodiment of the invention the first limit L1 is greater than or equal to 446 nm, preferably greater than or equal to 456 nm According to an embodiment of the invention, the second limit L2 is smaller than or equal to 477 nm, preferably smaller than or equal to 467 nm So as to further enhance the retinal Dopamine secretion the optical system according to the invention is arranged so that the average transmission T2 over the second zone Z2 is greater than the average transmission T1 and T3 over the first and third zones Z1, Z3.

In particular, the inventors have observed significant effects on myopia progression when the average transmission in each zone are such as $T2 > 5*(T1+T3)/2$.

Having the average transmission T2 over the second zone Z2 greater than or equal to 75% provides as much light in the range of wavelengths corresponding to the second zone as possible to the wearer's eyes. Thus, increasing the retinal Dopamine secretion of the wearer and reducing myopia progression of the wearer's eyes.

So as to provide a good protection of the eyes of the wearer, the average transmission T1 in the first zone may be smaller than the average transmission T3 in the third zone Z3. Indeed, the smaller wavelengths corresponding to the blue part of natural light are the most harmful for the wearer's eyes.

Depending on the use of the optical system and/or the choice of the wearer the average transmissions T1 and T3 over the first and third zones Z1 and Z3 may be different.

According to different embodiments of the invention, the average transmission T1 over the first zone Z1 may be:
  greater than or equal to 43% and smaller than or equal to 70%, so as to provide an optical system adapted for low luminosity environments,
  greater than or equal to 18% and smaller than or equal to 42%, so as to provide an optical system adapted for average luminosity environments,
  greater than or equal to 8% and smaller than or equal to 17%, so as to provide an optical system adapted for high luminosity environments, in an advantageous embodiment the first zone Z1 is splitted in a first sub-zone Z1a and a second sub-zone Z1b. The first sub-zone Z1a is from 380 nm to 400 nm and the average transmission T1a over the sub-zone Z1a T1a is smaller than 0.5%. The second sub-zone Z1b is from 400 nm to the first limit L1, greater than or equal to 3% and smaller than or equal to 7%, so as to provide an optical system adapted for very high luminosity environments.

According to different embodiments of the invention, the average transmission T3 over the third zone Z3 may be:

greater than or equal to 43% and smaller than or equal to 70%, so as to provide an optical system adapted for low luminosity environments, greater than or equal to 18% and smaller than or equal to 42%, so as to provide an optical system adapted for average luminosity environments, greater than or equal to 8% and smaller than or equal to 17%, so as to provide an optical system adapted for high luminosity environments, greater than or equal to 3% and smaller than or equal to 7%, so as to provide an optical system adapted for very high luminosity environments.

According to an embodiment of the invention, the optical system may be arranged so as to have a transmission pattern comprising more than 3 zones, in particular the transmission pattern may comprise more than one zone having a great average transmission. In such case, all odd number zones follow of the first and third zones Z1 and Z3 characteristics while the even numbers follow the characteristics of the second zone Z2.

As indicated previously, the optical system according to the invention has several effects on the visual system.

First, as any solar system, the optical system according to the invention results in an increase of the pupil size to keep a relatively constant retinal illuminance.

Secondly, as a consequence of increase of pupil size, the amount of light for the specific band of wavelengths corresponding to the second zone Z2 increases as a function of increase of the pupil diameter.

The result of such increase of transmission for wavelengths corresponding to the second zone Z2 is an increase of Dopamine synthesis (compared to not wearing the optical system according to the invention while in high luminance environment), resulting in a slow-down of myopia progression. Moreover, the lens will protect the eye against harmful wavelengths, in particular corresponding to the first zone Z1.

The optical system according to the invention may be a pair of optical lenses or a pair of an ophthalmic lenses, for example a pair of progressive addition lenses, or a pair of spectacle lenses, or a pair of contact lenses or a pair of intraocular lenses.

The invention further relates to the use of the optical system according to the invention to slow down myopia progression of the wearer, in particular of children.

The optical system according to the invention may comprise a photochromic function, i.e. the average transmissions in the different zones may vary based on the amount and/or intensity of the light received by the optical system at different wavelengths.

The optical system according to the invention may comprise an electro-chromic function, i.e. the average transmissions in the different zones may be controlled by an electric signal.

According to an embodiment, the optical system may be arranged so that only one of the zones is controlled by either a photochromic or an electro-chromic function, for example the third zone.

The optical system according to the invention may be obtained by any means known from the skilled person.

For example, a pair of optical lenses according to the invention may be obtained by using a specific interference filter determined to match the specific transmission pattern.

An optical system according to the invention may also be achieved by combining a specific dye with an interference filter each component resulting mainly in the transmission of one zone.

An optical system according to the invention may also be achieved by carrying out means for absorbing light or means for reflecting light. For example, means for absorbing light are based on use of dye, pigment, or any absorber included within the optical system, at a substrate level (within the material of the optical system) and/or at a level of a functional coating on the front face and/or on the rear face of the optical system. For example, means for reflecting light comprise inorganic layers or organic/inorganic layers coated on the front face and/or the rear face of the optical system such as anti-reflection coating, mirror coating, pass-band coating, . . . .

For example the part of the transmission pattern corresponding to the first zone Z1 can be obtained either by a UVAPLAST 365 dye or by an interference filter, such as LVF-H High-pass Filter (Ocean Optics).

The part of the transmission pattern corresponding to the third zone Z3 can be obtained through a bluish dye (such as nk-1 from Nidek corp.) or using a low-pass interference filter such as LVF-L Low-pass Filter (Ocean Optics).

The invention further relates to a method for selecting an optical system according to the invention adapted for a wearer, in particular for a child.

The method comprises the steps of measuring the effect of different optical systems according to the invention on the size of the pupil of the wearer and of selecting the optical system having the greatest average transmission value over the first and third zones and for which the wearer's pupil diameter has increased of at least 0.5 mm when wearing the optical system.

Advantageously, the method according to the invention allows providing the most transparent optical system that has the desired effect of protecting against harmful wavelengths over the first and third zone while reducing the progression of myopia of the wearer.

According to an embodiment of the invention, the method of selected an optical system is carried out under luminance conditions close to the luminance conditions under which the wearer is to use the optical system. For example, if the optical system is to be used under very bright light conditions the method of selection can advantageously be carried out under such bright light conditions.

In a similar manner if the optical system is to be used under average light conditions the method of selection can advantageously be carried out under such average light conditions.

The invention has been described above with the aid of embodiments without limitation of the general inventive concept.

Many further modifications and variations will suggest themselves to those skilled in the art upon making reference to the foregoing illustrative embodiments, which are given

The invention claimed is:

1. An optical system comprising multiple filters or multiple dyes, having a transmission pattern comprising at least a first zone Z1 extending from 380 nm to a first limit L1 between the first zone Z1 and a second zone Z2, and a third zone Z3 extending from a second limit L2 between the second zone Z2 and the third zone Z3 to 780 nm, wherein the first limit L1 is greater than or equal to 436 nm and the second limit L2 is greater than the first limit L1 and smaller than or equal to 487 nm;

the average transmission values T1, T2, T3, in each zone Z1, Z2, Z3 are such as:

$$T2 > 5*(T1+T3)/2, \text{ with}$$

T1 the average transmission over the first zone Z1,
T2 the average transmission over the second zone Z2, and
T3 the average transmission over the third zone Z3,
T1 and T3 each being greater than or equal to 3% and each being smaller than 37%,
wherein the average transmission values T1 and T3 are selected such that $5*(T1+T3)/2 < 100\%$, and
wherein the transmission pattern is configured such that it provides non-zero transmission extending throughout the range of 380 nm to 780 nm.

2. The optical system according to claim 1, wherein the first limit L1 is greater than or equal to 446 nm.

3. The optical system according to claim 1, wherein the second limit L2 is smaller than or equal to 477 nm.

4. The optical system according to claim 1, wherein the average transmission T2 over the second zone Z2 is greater than or equal to 75%.

5. The optical system according to claim 1, wherein the average transmission T1 over the first zone Z1 is smaller than or equal to the average transmission T3 over the third zone Z3.

6. The optical system according to claim 1, wherein the average transmission T1 over the first zone Z1 is greater than or equal to 8% and smaller than 37%.

7. The optical system according to claim 1, wherein the average transmission T1 over the first zone Z1 is greater than or equal to 8% and smaller than or equal to 18%.

8. The optical system according to claim 1, wherein the average transmission T3 over the third zone Z3 is greater than or equal to 8% and smaller than 37%.

9. The optical system according to claim 1, wherein the average transmission T3 over the third zone Z3 is greater than or equal to 8% and smaller than or equal to 18%.

10. The optical system according to claim 1, wherein the optical system is an optical system selected among the list of optical systems consisting of optical lens, ophthalmic lens, spectacle lens, contact lens, intraocular lens.

11. A method for selecting an optical system adapted for a wearer, the method comprising the steps of:
forming a plurality of optical systems, each optical system of the plurality of optical systems being the optical system of claim 1;
measuring the effect of the different optical systems on the size of the pupil of the wearer; and
selecting the optical system from the plurality of optical systems having the greatest average transmission value over the first and third zones and for which the wearer's pupil diameter has increased by at least 0.5 mm when wearing the optical system.

12. A method to slow down myopia progression of a wearer, comprising:
wearing the optical system according to claim 1.

13. The optical system according to claim 1 for slowing down myopia progression of a wearer.

* * * * *